US006658298B2

United States Patent
Gruzdowich et al.

(10) Patent No.: US 6,658,298 B2
(45) Date of Patent: *Dec. 2, 2003

(54) METHOD OF BLOOD PRESSURE MODERATION

(75) Inventors: Gregory J. Gruzdowich, Carlsbad, CA (US); David D. Swenson, Carlsbad, CA (US); Thomas L. Grey, Carlsbad, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/150,570

(22) Filed: May 16, 2002

(65) Prior Publication Data

US 2002/0133210 A1 Sep. 19, 2002

Related U.S. Application Data

(63) Continuation of application No. 09/767,062, filed on Jan. 22, 2001, now Pat. No. 6,393,324, which is a continuation of application No. 09/307,272, filed on May 7, 1999, now Pat. No. 6,178,352.

(51) Int. Cl.$^7$ .................................................. A61N 1/04
(52) U.S. Cl. ........................................................ 607/44
(58) Field of Search ........................... 128/898; 600/372, 600/384, 386, 390; 607/44, 72

(56) References Cited

U.S. PATENT DOCUMENTS

| | | | |
|---|---|---|---|
| 4,566,064 A | | 1/1986 | Whitaker |
| 4,981,146 A | * | 1/1991 | Bertolucci .................. 128/802 |
| 5,707,400 A | | 1/1998 | Terry, Jr. et al. .............. 607/44 |
| 5,727,558 A | | 3/1998 | Hakki et al. ................. 128/672 |
| 5,891,181 A | | 4/1999 | Zhu ............................ 607/44 |
| 5,891,182 A | | 4/1999 | Fleming ....................... 607/50 |
| 6,178,352 B1 | * | 1/2001 | Gruzdowich et al. .......... 607/44 |
| 6,393,324 B2 | * | 5/2002 | Gruzdowich et al. .......... 607/44 |

* cited by examiner

Primary Examiner—Jeffrey R. Jastrzab
Assistant Examiner—Frances P. Oropeza
(74) Attorney, Agent, or Firm—K. David Crockett, Esq.; Crockett & Crockett

(57) ABSTRACT

A method of controlling the blood pressure in a patient with high blood pressure or low blood pressure utilizing a non-invasive nerve stimulation device applied to the wrist.

8 Claims, 1 Drawing Sheet

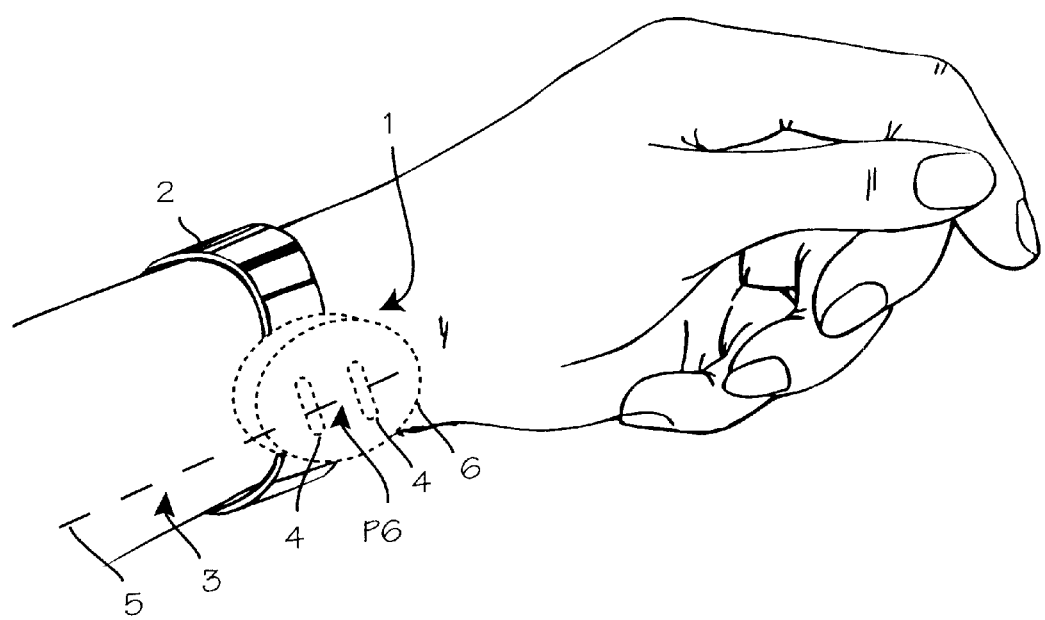

METHOD OF BLOOD PRESSURE MODERATION

RELATED PATENTS

This application is a continuation of U.S. application Ser. No. 09/767,062 filed Jan. 22, 2001, now U.S. Pat. No. 6,393,324, which is a continuation of U.S. application Ser. No. 09/307,272 filed May 7, 1999, now U.S. Pat. No. 6,178,352.

FIELD OF THE INVENTIONS

This invention relates to moderation of blood pressure.

BACKGROUND OF THE INVENTIONS

High blood pressure and low blood pressure are usually treated with drugs. Several proposals have been made to treat blood pressure with electrical stimulus applied to the body. For example, Terry, et al, Treating Refractory Hypertension By Nerve Stimulation, U.S. Pat. No. 5,707,400 (Jan. 13, 1998) proposes implantation of an electrical coil around the vagus nerve, which runs superficially through the neck, and stimulation of the vagus nerve to lower high blood pressure. Zhu, Blood Pressure Depressor, U.S. Pat. No. 5,891,181 (Apr. 6, 1999) proposes electrical stimulation of nerves in the ear lobe to lower blood pressure. Pomeranz, et al, Electrotherapy Acupuncture Apparatus and Method, U.S. Pat. No. 4,566,064 (Dec. 3 1985) mentions blood pressure as an indication for electro-acupuncture, but does not mention any point of application.

Bertolucci, Nausea Control Device, U.S. Pat. No. 4,981,146, Jan. 1, 1991, describes a nausea control device in the form of a watch-like housing attachable to the human wrist by an adjustable attachment band. The device uses non-invasive nerve stimulation whereby electricity is passed through two electrodes to stimulate nerves located on the ventral side of the wrist (this anatomical position is sometimes referred to as the palmar side of the wrist). The treatment provided by the device is sometimes referred to as electro-acupuncture, which is a form of acupuncture, and the ventral site of application is referred to in the acupuncture art as the P6 point, pericardium 6 point, or master point of the pericardium meridian (sometimes referred to as the vascular meridian). A primary object of the invention is to provide a non-chemical, non-invasive, painless and inexpensive method of alleviating nausea. It is also portable, self-contained and convenient to the patient. Electrical pulse repetition rate of approximately 70 pulses per second and a pulse width of 80 microseconds has been found to provide effective relief of nausea in a patient. Our currently preferred electrical pulse pattern comprises about 350 microsecond pulse width at about 31 pulses per second at power levels of about 10–35 milli-amps peak pulse height. Thus a wide range of pulse patterns may be used in non-invasive nerve stimulation devices.

Recently, we have discovered that the application of electrical stimulus to the wrist, on the ventral side of the wrist and near the P6 acupuncture point, effectively moderates blood pressure.

SUMMARY

The method described below employs use of the device described in Bertolucci, Nausea Control Device, U.S. Pat. No. 4,981,146, Jan. 1, 1991, and similar devices for moderation of blood pressure in patients suffering from high or low blood pressure. A patient desiring to moderate his or her blood pressure places a pair of electrodes on the inside (ventral side) of the wrist, and applying electrical stimulation to the wrist through these electrodes. This has the effect of moderating blood pressure in the patient, lowering high blood pressure and raising low blood pressure. The electrodes, pulse generating circuitry, and power supply are most conveniently packaged in a wrist-watch like housing which is held to the wrist with a watch band or with adhesive on the device. The technique accomplished by the device is referred to as electro-acupuncture or non-invasive nerve stimulation.

DETAILED DESCRIPTION OF THE FIGURE

The FIGURE illustrates placement of an electroacupuncture over the P6 acupuncture point on the human wrist.

DETAILED DESCRIPTION OF THE INVENTIONS

Our discovery derives from speculation regarding the potential biological effects of electrical stimulation of the P6 acupuncture point beyond the suppression of nausea described in the Bertolucci patent. Volunteer patients were tested for blood pressure, with two blood pressure measurements taken about five minutes apart. All subjects had the ReliefBand® NST™ non-invasive nerve stimulation device placed on their left wrist, as shown in the figure, for approximately thirty minutes. The ReliefBand® NST™ non-invasive nerve stimulation device 1 was secured with strap 2 to the ventral side of the wrist 3 such that the pair of electrodes 4 were disposed over the median nerve 5 (indicated by the phantom line) in contact with the skin in the vicinity of the P6 acupuncture point. The electrodes are on the underside of the housing 6, the required battery and control electronics are housed within the housing, and input mechanisms are located on the outer face of the housing. After thirty minutes of treatment, the blood pressure of each patient was measured twice (measurements were separated by five minutes interval). A statistically significant reduction in blood pressure was observed in the group. In some patients, blood pressure was lowered by as much as ten percent. One patient whose blood pressure was considered abnormally low was increased toward the normal range (systolic pressure of 100 mmHG was raised approximately 10%). Patients with normal blood pressure at the start of the test were not observed to have significant changes in their blood pressure after application of the stimulation.

The mechanism of action is not thoroughly understood. However, we expect that both high blood pressure and low blood pressure conditions should be moderated by application of the same electrical stimulation to the ventral side of the wrist (or the P6 acupuncture point or the median nerve). The technique accomplished by the device is referred to as electro-acupuncture or non-invasive nerve stimulation, and has components of acupuncture effect and acupressure. While we used the ReliefBand® NST™ non-invasive nerve stimulation device, any suitable means of applying electrical stimulation to the median nerve should work to moderate blood pressure. Also, while we applied the electrical stimulation to the median nerve at its superficial route through the wrist, stimulation of the median nerve along its entire course should provide similar benefits.

While the preferred embodiments of the methods have been described in reference to the environment in which they were developed, they are merely illustrative of the principles of the inventions. Other embodiments and configurations may be devised without departing from the spirit of the inventions and the scope of the appended claims.

We claim:

1. A method of increasing blood pressure in a patient with low blood pressure, said method comprising the steps of:

mounting a non-invasive nerve stimulation device onto the ventral side of the wrist;

generating a stimulation signal; and delivering the stimulation signal to the ventral side of the wrist to increase blood pressure in a patient.

2. A method of increasing blood pressure in a patient with low blood pressure, said method comprising the steps of:

mounting at least one electrode onto the ventral side of the wrist;

generating a stimulation signal; and delivering the stimulation signal to said at least one electrode to stimulate the ventral side of the wrist to increase blood pressure in a patient.

3. The method of claim 2 wherein said mounting step includes providing a wristwatch-like housing carrying the at least one electrode, and providing securing means for mounting the housing onto the wrist, with the housing having a circuit means for generating the stimulation signal encased within the housing.

4. The method of claim 2 wherein said delivering step comprises delivering an intermittent stimulation signal.

5. The method of claim 2 wherein said delivering step comprises delivering a continuous stimulation signal.

6. A method of controlling the blood pressure in a patient with low blood pressure by remotely stimulating the patient's median nerve and associated nerve structures with electrical energy.

7. A method of controlling the blood pressure in a patient with low blood pressure comprising the steps of:

mounting a non-invasive nerve stimulation device onto the wrist;

generating an electrical stimulation signal; and delivering the electrical stimulation signal to the wrist.

8. A method of controlling the blood pressure in a patient with low blood pressure, said method comprising the steps of:

applying an electro-acupuncture device to the wrist;

stimulating the wrist with the electro-acupuncture device.

* * * * *